(12) United States Patent
Kosley et al.

(10) Patent No.: US 8,053,458 B2
(45) Date of Patent: Nov. 8, 2011

(54) DIPYRAZOLE COMPOUNDS AND THEIR USE AS CENTRAL NERVOUS SYSTEM AGENTS

(75) Inventors: Raymond W. Kosley, Bridgewater, NJ (US); Douglas MacDonald, Los Angeles, CA (US); Rosy Sher, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 939 days.

(21) Appl. No.: 11/855,521

(22) Filed: Sep. 14, 2007

(65) Prior Publication Data

US 2008/0090872 A1   Apr. 17, 2008

Related U.S. Application Data

(63) Continuation of application No. PCT/US2006/009348, filed on Mar. 15, 2006.

(60) Provisional application No. 60/662,195, filed on Mar. 16, 2005.

(51) Int. Cl.
*A61K 31/455* (2006.01)
*C07D 231/26* (2006.01)
(52) U.S. Cl. ............ 514/404; 514/407; 548/365.4
(58) Field of Classification Search ......... 514/404, 514/407; 548/365.4
See application file for complete search history.

(56) References Cited

FOREIGN PATENT DOCUMENTS
EP        0976744        2/2000
WO   WO 2005/040110   5/2005

OTHER PUBLICATIONS

Kumar et al. "The structure of compounds . . . " CA 123:255894 (1995).*
Rachedi et al. "reaction of 4-hydroxyl . . . " Ca 115:114412 (1991).*
Borrell et al. "Design and synthesis of two pyrazole . . . " Molecular diversity v.8, p. 147-157 (2004).*
Bendaas et al. "Synthesis of bipyrazoles . . . " CASREACT 132:166166 (1999).*
Xie et al. "Synthesis and crystal . . . " J. Hetercyclic Chem. v.45, p. 1485-1488 (2008).*
DEas et al. "Heterocyclic fungicides" CA90:121480 (1979).*
Obara et al. "Bipyrazole . . . " CA133:232875 (2000).*
Ohara et al. "Preparation of bipyrazole . . . " CA130:38378(1998).*
Federal Registry p. 1-34, Sep. 1, 2010.*
Cantos, A., et. al., Synthesis of Pyrano{4,3-c}Pyrazol-4(1H)-Ones and -4(2H)-ones from Dehydroacetic Acid. Homo- and Heteronuclear Selective NOE Measurements for Unambiguous Structure Assignment, Bull. Chem. Soc. Jpn. vol. 60, p. 4425-4431 (1987).
Crippa, G.B., et. al., Ricerche Sul Chimismo Del Nucleo Pirazolico Trasposizione Da Bis-4-5'- in Bis-4-4'Pirazolene, Gazz. Chem. Ital. vol. 71, (1941), pp. 574-580.
Singh, S. P., et. al., A 1H and 13 C NMR Study of the Structure and Tautomerism of 4-Pyrazolylpyrazolinones, Journal of Heterocyclic Chemistry, vol. 27, (1990), pp. 865-870.
Singh, S. P., et. al., C-C Bond Cleavage Studies in Bipyrazoles: A Convenient Synthesis of Pyrazolo-5-ols, Synthetic Communications, vol. 35, pp. 611-619, (2005).
Singh, S. P., et. al., Reaction of 1-[5-Hydroxy-3-Methyl-1-(2-Thiazolyl)-4-Pyrazolyl]- 1,3-Butanediones With Phenyl and Heterocyclic Hydrazines: A Convenient Synthesis of 4,5' -Bipyrazoles, Indian Journal of Heterocyclic Chemistry vol. 3, (1993), pp. 5-8.
Singh, S.P., et. al., Mass Spectra of Some 3, 3'-Dimethyl (4,5-Bipyrazol)-5-Ols, Organic Mass Spectrometry, vol. 20, No. 7, (1985) pp. 484-485.
Interchim Intermediates, Database Chemcats (2005) Order No. 10E-969, 10E-914, 10E-973, 10E-944, 10E-974, 10E-921, 10E-937, 7E-913, and RN 303997-19-5, abstract.

* cited by examiner

*Primary Examiner* — Celia Chang
(74) *Attorney, Agent, or Firm* — Kelly L. Bender; Craig M. Bell

(57) ABSTRACT

The present invention is directed to dipyrazole compounds of formula I and their pharmaceutically acceptable salts, stereoisomers, tautomers, or solvates thereof. Novel compounds include those of formula I.

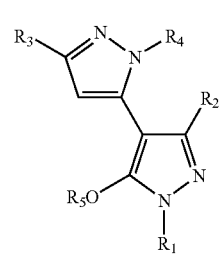

The compounds of this invention modulate AMPA and NMDA receptor function, and therefore are useful as pharmaceutical agents, especially for the treatment of neuropsychiatric disorders.

16 Claims, No Drawings

US 8,053,458 B2

DIPYRAZOLE COMPOUNDS AND THEIR USE AS CENTRAL NERVOUS SYSTEM AGENTS

CROSS-REFERENCE TO RELATED APPLICATIONS

This application is a continuation of International Patent Application No. PCT/US2006/009348 filed on Mar. 15, 2006 which is incorporated herein by reference in its entirety which also claims the benefit of priority of U.S. Provisional Application No. 60/662,165 filed on Mar. 16, 2005.

FIELD OF THE INVENTION

The present invention relates to novel dipyrazole compounds, compositions, and methods for the treatment and/or prevention of neuropsychiatric disorders that result primarily from dysfunction at the glutamate receptors AMPA and NMDA.

BACKGROUND OF THE INVENTION

Glutamate is the most abundant excitatory neurotransmitter in the mammalian central nervous system (CNS) and mediates the fast and slow neurotransmission responsible for such normal neurophysiological processes as memory acquisition and processing, and synaptic plasticity. Postmortem and pharmacological findings strongly implicate dysregulation of glutamate neurotransmission in the pathophysiology of several neuropsychiatric disorders including schizophrenia, Alzheimer disease, Parkinson disease, Huntington disease, epilepsy, attention-deficit hyperactivity disorder, AIDS-related dementia, neuropathic pain, depression, mild cognitive impairment, learning and memory disorders, and others (Lehohla, et al., *Metab Brain Dis,* 2004; Coyle, et al., *Ann. NY Acad. Sci.,* 2003; Coyle, et al., *Curr. Drug Targets CNS Neurol. Disord.,* 2002; Krystal, et al., *Arch Gen Psychiatry,* 2002; Dingledine et al., *Pharmacol. Rev.,* 1999; and Ozawa, et al., *Prog. Neurobiol.,* 1998).

Glutamate neurotransmission is mediated by three ionotropic glutamate receptors. These receptors are cation-specific ion channels which regulate fast synaptic neurotransmission. The ionotropic glutamate receptors have been classified into three types: the alpha-amino-3-hydroxy-5-methylisoxazole-4-propionic acid (AMPA) receptors, the kainic acid (KA) receptors, and the N-methyl-D-aspartate (NMDA) receptors based on their unique pharmacological, electrophysiological and biochemical properties (Nakanishi, *Science,* 1992). Furthermore, each of these ionotropic glutamate receptors is made up of multiple heteromeric subunits, contributing to receptor heterogeneity in different tissues (Ozawa, et al., Prog Neurobiol, 1998). However, each of the ionotropic glutamate receptors contain predominant subunits, some requisite for functionality and thought to be most responsible for the regulation of function.

Regulation of the ionotropic glutamate receptors is partly achieved through phosphorylation of specific tyrosine, threonine and serine residues by several kinases and, conversely, through de-phosphorylation of those residues by specific phosphatases (Carvalho, et al., *Neurochem. Res.,* 2000 and Swope, et al., Adv Second Messenger Phosphoprotein Res. 1999). The phosphorylation state of receptor subunits plays a critical role in receptor activity. For example, NMDA receptors are regulated by several kinases and phosphatases acting on its NR1 subunit. Protein kinase C (PKC), and cAMP-dependent protein kinase (PKA) have been shown to phosphorylate serine residues 896 and 897 of the NR1 subunit, respectively (Tingley, et al., *J. Biol. Chem.,* 1997 and Snyder, et al., *Neuropharmacology,* 2003). Likewise, AMPA receptors are regulated by several kinases and phosphatases acting on the GluR1 subunit; PKA phosphorylates serine residue 845 (Roche, et al., *Neuron* 16: 1179-1188, 1999; Wang, et al., *Science* 253: 1132-1135, 1991). Protein phosphatase I (PP1) dephosphorylates these serine residues, thus leading to a molecular switch for receptor activity.

Spinophilin (also named Neurabin II) is a scaffold protein, which is enriched in the dendritic spines of CNS neurons that serve as the major site of glutamatergic synapses in the brain (Allen, et al., *Proc. Natl. Acad. Sci. USA,* 1997; Hsieh-Wilson, et al., *Biochemistry,* 1999). Spinophilin was originally identified based on its ability to bind F-actin and protein phosphatase I (PP1). The interaction of spinophilin with PP1 is especially important for the function of ionotropic glutamate receptors as spinophilin acts as a modulator of glutamatergic synaptic neurotransmission by regulating PP1's ability to dephosphorylate the ionotropic glutamate receptors via localization. Evidence for such a function has been demonstrated using voltage whole-cell recordings of kainic acid-induced rundown of AMPA currents in individual acutely dissociated prefrontal cortical neurons (Yan, et al., *Nature Neurosci.* 1999). In these experiments, agonist-induced rundown of kainic-acid-evoked currents was inhibited by a peptide corresponding to the PP1 binding domain of spinophilin, but not by the same peptide containing a point mutation, thus indicating that when spinophilin no longer interacts with PP1, AMPA receptors (in this example) are no longer dephosphorylated to reduce function; therefore, they remain more active.

In order to discover small molecule compounds that would mimic the action of the spinophilin peptide described above, a novel protein interaction assay between PP1 and spinophilin was utilized to discover inhibitors of binding. These compounds were then evaluated in a whole-cell voltage clamp assay for the ability to inhibit the agonist-induced rundown of AMPA currents and for modulation of NMDA-evoked currents.

Thus, compounds discovered here should have utility in the treatment of several neurospychiatric disorders which have been linked to the dysfunction of glutamate neurotransmission.

SUMMARY OF THE INVENTION

The present invention is a compound of formula I:

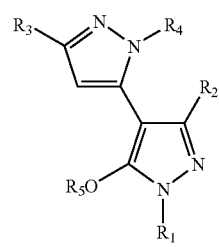

or a stereoisomer or pharmaceutically acceptable salt thereof, wherein:
$R_1$ is selected from the group consisting of aryl, benzyl, $C_{3-8}$cycloalkyl, $C_{1-10}$alkyl, $C_{3-8}$cycloalkyl-$C_{1-6}$alkyl, hetero-aryl, aryl-carbonyl, aryl$C_{1-6}$alkyl-$C_{3-8}$cycloalkylcarbonyl, $C_{1-10}$alkylcarbonyl, hetero-arylcarbonyl and

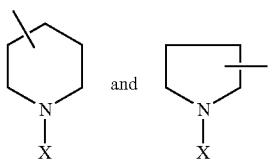

wherein X is hydrogen, benzyl, arylC$_{2-6}$alkyl, C$_{3-8}$cycloalkyl, C$_{1-10}$alkyl, or C$_{3-8}$cycloalkylC$_{1-16}$alkyl;

wherein said aryl, benzyl, or hetero-aryl is optionally substituted with one or more substituents each independently selected from the group consisting of C$_{3-8}$cycloalkyl-C$_{1-6}$ alkyl C$_{1-6}$alkyl, C$_{1-6}$ perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, or aryl;

R$_2$ is selected from the group consisting of C$_{1-6}$alkyl, C$_{3-8}$cycloalkyl, and aryl wherein said aryl is optionally substituted with one or more substituents each independently selected from C$_{1-6}$alkyl, C$_{1-6}$ perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_3$ is selected form the group consisting of aryl, C$_{3-8}$cycloalkyl, C$_{1-6}$alkyl and hetero-aryl wherein said aryl or hetero-aryl is optionally substituted with one or more substituents each independently selected from C$_{1-6}$alkyl, C$_{1-6}$perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_4$ is selected form the group consisting of H, aryl, arylC$_{2-6}$ alkyl, benzyl, hydroxyC$_{2-6}$alkyl C$_{1-6}$perfluoroalkyl, C$_{3-8}$cycloalkyl and C$_{1-6}$alkyl wherein said aryl or benzyl is optionally substituted with one or more substituents each independently selected from C$_{1-6}$alkyl, C$_{1-6}$perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_5$ is H, C$_{1-6}$alkyl, or C$_{3-8}$cycloalkyl; and with the proviso that
(a) when R$_1$ and R$_4$ are phenyl or 4-chlorophenyl, and R$_5$ is hydrogen, then R$_2$ and R$_3$ cannot be simultaneously methy
(b) when R$_1$ is phenyl or 4-chlorophenyl and R$_4$ and R$_5$ are hydrogen then R$_2$ and R$_3$ are other than methyl simultaneously.

The present invention is also directed to pharmaceutical compositions of formula (I).

Another aspect of this invention is disclosed a method of treating a neuropsychiatric disorder responsive to modulation of AMPA and NMDA receptors, comprising administering to a mammal in need of said treatment a therapeutically effective amount of a compound of formula I

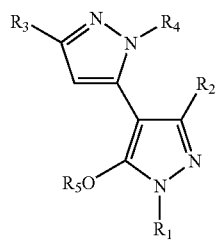

I or a stereoisomer or pharmaceutically acceptable salt thereof, wherein:

R$_1$ is selected from the group consisting of aryl, benzyl, C$_{3-8}$cycloalkyl, C$_{1-10}$alkyl, C$_{3-8}$cycloalkylC$_{1-6}$alkyl, hetero-aryl, arylcarbonyl, arylC$_{1-6}$alkylC$_{3-8}$cycloalkylcarbonyl, C$_{1-10}$alkylcarbonyl, hetero-arylcarbonyl and

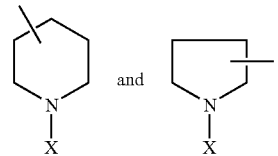

wherein X is hydrogen, benzyl, arylC$_{2-6}$alkyl, C$_{3-8}$cycloalkyl, C$_{1-10}$alkyl, or C$_{3-8}$cycloalkylC$_{1-6}$alkyl;

wherein said aryl, benzyl, or hetero-aryl is optionally substituted with one or more substituents each independently selected from C$_{1-6}$alkyl, C$_{1-6}$ perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, or aryl;

R$_2$ is selected from the group consisting of C$_{1-6}$alkyl, C$_{3-8}$cycloalkyl, and aryl wherein said aryl is optionally substituted with one or more substituents each independently selected from C$_{1-6}$alkyl, C$_{1-6}$perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_3$ is selected form the group consisting of aryl, C$_{3-8}$cycloalkyl, C$_{1-6}$alkyl and hetero-aryl wherein said aryl or hetero-aryl is optionally substituted with one or more substituents each independently selected from C$_{1-6}$alkyl, C$_{1-6}$perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_4$ is selected form the group consisting of H, aryl, arylC$_{2-6}$alkyl, benzyl, hydroxyC$_{2-6}$alkyl C$_{1-6}$ perfluoroalkyl, C$_{3-8}$cycloalkyl and C$_{1-6}$alkyl wherein said aryl or benzyl is optionally substituted with one or more substituents each independently selected from C$_{1-6}$alkyl, C$_{1-6}$perfluoroalkyl, halogen, hydroxy, C$_n$H$_x$F$_{y-6}$alkoxy wherein n is 1-4, x is 0-8, y is 1-9 and x+y is 2n+1, C$_1$-C$_6$alkoxy, nitro, aryl, or alkoxy;

R$_5$ is H, C$_{1-6}$alkyl, or C$_{3-8}$cycloalkyl.

DETAILED DESCRIPTION OF THE INVENTION

The terms as used herein have the following meanings:

As used herein, the expression "C$_{1-6}$ alkyl" used alone or in combination with other terms means an alkyl (or alkylene as appropriate), straight or branched-chain and includes methyl and ethyl groups, and straight-chained or branched propyl, butyl, pentyl and hexyl groups. Particular alkyl groups are methyl, ethyl, n-propyl, isopropyl and tert-butyl. Derived expressions such as "C$_{1-6}$alkoxy", "C$_{1-6}$alkoxyC$_{1-6}$alkyl", "hydroxyC$_{1-6}$alkyl", "C$_{1-6}$alkylcarbonyl", "C$_{1-6}$alkoxycarbonylC$_{1-6}$alkyl", "C$_{1-6}$alkoxycarbonyl", "aminoC$_{1-6}$alkyl", "C$_{1-6}$alkylcarbamoylC$_{1-6}$alkyl", "C$_{1-6}$dialkylcarbamoylC$_{1-6}$alkyl" "mono- or di-C$_{1-6}$alkylaminoC$_{1-6}$alkyl", aminoC$_{1-6}$alkylcarbonyl", "diphenylC$_{1-6}$alkyl", "phenylC$_{1-6}$alkyl", "phenylcarboylC$_{1-6}$alkyl" and "phenoxyC$_{1-6}$alkyl" are to be construed accordingly.

As used herein, the expression "C$_{2-6}$alkenyl" includes ethenyl and straight-hained or branched propenyl, butenyl, pentenyl and hexenyl groups. Similarly, the expression "C$_{2-6}$ alkylnyl" includes ethynyl and propynyl, and straight-chained or branched butynyl, pentynyl and hexynyl groups.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. The derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkyl$C_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein "halogen" or "halo" means chloro, fluoro, bromo, and iodo.

As used herein the expression "carbamoyl" means an —NC(O)— group where the radical is bonded at two positions connecting two separate additional groups.

As used herein "aryl" represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

As used herein "hetero-aryl" represents a heterocyclic aromatic ring system containing one or more heteroatoms selected from nitrogen, oxygen and sulfur such as furanyl, thiophenyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Hetero-aryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

As used herein "heterocyclyl" represents a saturated 3 to 8 membered ring containing one or more heteroatoms selected from nitrogen, oxygen and sulfur. Representative examples are pyrrolidyl, piperidyl, piperazinyl, morpholinyl, thiomorpholinyl, aziridinyl, tetrahydrofuranyl and the like.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, 'treat' or 'treating' means any treatment, including but not limited to, alleviating symptoms, eliminating the causation of the symptoms either on a temporary or permanent basis, or to preventing or slowing the appearance of symptoms and progression of the named disease, disorder or condition.

"Therapeutically effective amount" means an amount of the compound which is effective in treating the named disorder or condition.

As used herein, "patient" means any warm blooded animal, such as for example, rats, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

As used in the examples and preparations that follow, the terms used therein shall have the meanings indicated: "kg" refers to kilograms, "g" refers to grams, "mg" refers to milligrams, "μg" refers to micrograms, "pg" refers to picograms, "mol" refers to moles, "mmol" refers to millimoles, "nmole" refers to nanomoles, "L" refers to liters, "mL" or "ml" refers to milliliters, "μL" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "MP-carbonate" refers to a macroporous polystyrene anion exchange resin that is a resin bound equivalent to tetraalkylammonium carbonate, "brine" refers to a saturated aqueous sodium chloride solution, "M" refers to molar, "mM" refers to millimolar, "µM" refers to micromolar, "nM" refers to nanomolar, "TLC" refers to thin layer chromatography, "HPLC" refers to high performance liquid chromatography, "HRMS" refers to high resolution mass spectrum, "CIMS" refers to chemical ionization mass spectrometry, "$t_R$" refers to retention time, "lb" refers to pounds, "gal" refers to gallons, "L.O.D." refers to loss on drying, "µCi" refers to microcuries, "i.p." refers to intraperitoneally, "i.v." refers to intravenously.

In one aspect of this invention there is disclosed novel compounds having the general structure as shown in formula I:

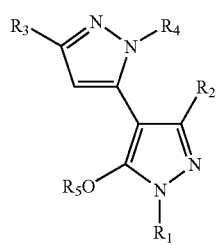

or a stereoisomer or pharmaceutically acceptable salt thereof, wherein:

$R_1$ is selected from the group consisting of aryl, benzyl, $C_{3-8}$cycloalkyl, $C_{1-10}$alkyl, $C_{3-8}$cycloalkyl$C_{1-6}$alkyl, hetero-aryl, arylcarbonyl, aryl$C_{1-6}$alkyl$C_{3-8}$cycloalkylcarbonyl, $C_{1-10}$alkylcarbonyl, hetero-arylcarbonyl and

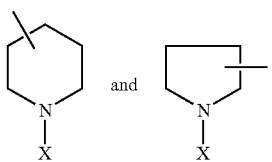

wherein X is hydrogen, benzyl, aryl$C_{2-6}$alkyl, $C_{3-8}$cycloalkyl, $C_{1-10}$alkyl, or $C_{3-8}$cycloalkyl$C_{1-6}$alkyl;

wherein said aryl, benzyl, or hetero-aryl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, or aryl;

$R_2$ is selected from the group consisting of $C_{1-6}$alkyl, $C_{3-8}$cycloalkyl, and aryl wherein said aryl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy;

$R_3$ is selected form the group consisting of aryl, $C_{3-8}$cycloalkyl, $C_{1-6}$-alkyl and hetero-aryl wherein said aryl or hetero-aryl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy;

$R_4$ is selected form the group consisting of H, aryl, aryl$C_{2-6}$alkyl, benzyl, hydroxy$C_{2-6}$alkyl $C_{1-6}$perfluoroalkyl, $C_{3-8}$cycloalkyl and $C_{1-6}$alkyl wherein said aryl or benzyl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy; $R_5$ is H, $C_{1-6}$alkyl, or $C_{3-8}$cycloalkyl; and with the proviso that
(a) when $R_1$ and $R_4$ are phenyl or 4-chlorophenyl, and $R_5$ is hydrogen then $R_2$ and $R_3$ are other than methyl simultaneously;
(b) when $R_1$ is phenyl or 4-chlorophenyl and $R_4$ and $R_5$ are hydrogen then $R_2$ and $R_3$ are other than methyl simultaneously.

In a further embodiment of the compound of formula I of this invention, $R_1$ is selected from the group consisting of aryl, benzyl, $C_{3-8}$cycloalkyl, $C_{1-10}$alkyl, aryl$C_{1-6}$alkyl and

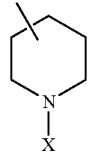

wherein X is benzyl, $R_2$ and $R_3$ are $C_{1-6}$alkyl and $R_5$ is hydrogen or $C_{1-6}$alkyl.

In another embodiment of the compound of formula I of this invention, $R_1$ is aryl, $R_2$ and $R_3$ are $C_{1-6}$alkyl, $R_4$ is hydrogen, and $R_5$ is hydrogen or $C_{1-6}$alkyl.

Representative examples of compounds of this embodiment of the compound of formula I are selected from the group consisting of: 2'-(2-Fluoro-phenyl)-5,5'-dimethyl-2H, 2'H-[3,4']bipyrazolyl-3'-ol, 2'-(4-isopropyl-phenyl)-5,5'-dimethyl-2H,2'H-[3,4']bipyrazolyl-3'-ol, 2'-(4-Fluoro-phenyl)-5,5'-dimethyl-2H,2'H-[3,4']bipyrazolyl-3'-ol, 5,5'-Dimethyl-2'-(4-trifluoromethyl-phenyl)-2H,2'H-[3,4'] bipyrazolyl-3'-ol, 5,5'-Dimethyl-2'-(4-methoxy-phenyl)-2H, 2'H-[3,4']bipyrazolyl-3'-ol, 2'-(3-Fluoro-phenyl)-5,5'-dimethyl-2H,2'H-[3,4']bipyrazolyl-3'-ol, 2'-(2-Methyl-phenyl)-5,5'-dimethyl-2H, 2'H-[3,4']bipyrazolyl-3'-ol, 5,5'-Dimethyl-2'-(4-trifluoromethoxy-phenyl)-2H,2'H-[3,4'] bipyrazolyl-3'-ol, 5,5'-Dimethyl-2'-(4-methyl-phenyl)-2H, 2'H-[3,4']bipyrazolyl-3'-ol, 5,5'-Dimethyl-2'-(3-methyl-phenyl)-2H,2'H-[3,4']bipyrazolyl-3'-ol, 5,5'-Dimethyl-2'-(2-ethyl-phenyl)-2H,2'H-[3,4']bipyrazolyl-3'-ol, 5,5'-Dimethyl-2'-(3,4-dichloro-phenyl)-2H, 2'H-[3,4']bipyrazolyl-3'-ol, 5,5'-Dimethyl-2'-(3-chlorophenyl)-2H,2'H-[3,4']bipyrazolyl-3'-ol, 2'-(4-tert-Butyl-phenyl)-5,5'-dimethyl-2H,2'H-[3,4']bipyrazolyl-3'-ol, 5,5'-Dimethyl-2'-(3-trifluoromethyl-phenyl)-2H,2'H-[3,4']bipyrazolyl-3'-ol, and 5'-Methoxy-5,3'-dimethyl-1'-phenyl-2H,1'H-[3,4']bipyrazolyl.

In a further embodiment of the compound of formula I of this invention, $R_1$ is aryl, $R_2$ and $R_3$ are $C_{1-6}$alkyl, $R_4$ is aryl$C_{2-6}$alkyl, or benzyl and $R_5$ is hydrogen or $C_{1-6}$alkyl.

Representative examples of compounds of this embodiment of the compound of formula I are selected from the group consisting of: 5,5'-Dimethyl-2-phenethyl-2'-phenyl-2H,2'H-[3,4']bipyrazolyl-3'-ol, 2-Benzyl-5,5'-dimethyl-2'-phenyl-2H,2'H-[3,4']bipyrazolyl-3'-ol, and 2-Benzyl-5'- methoxy-5,3'-dimethyl-1'-phenyl-2H,1'H-[3,4']bipyrazole, and 2-(3-Hydroxy-benzyl)-5,5'-dimethyl-2'-phenyl-2H,2'H-[3,4']bipyrazolyl-3'-ol.

In another embodiment of the compound of formula I of this invention, $R_1$ is aryl, $R_2$ and $R_3$ are $C_{1-6}$alkyl, $R_4$ is hydroxy$C_{1-6}$alkyl $C_{1-6}$perfluoroalkyl, $C_{3-8}$cycloalkyl or $C_{1-6}$alkyl and $R_5$ is hydrogen.

Compounds exemplary of this embodiment of the compound of formula I are selected from the group consisting of: 5,5'-Dimethyl-2'-phenyl-2-(2,2,2-trifluoro-ethyl)-2H,2'H-[3,4']bipyrazolyl-3'-ol, 2-Cyclohexyl-5,5'-dimethyl-2'-phenyl-2H,2'H-[3,4']bipyrazolyl-3'-ol, 2-(2-Hydroxy-ethyl)-5,5'-dimethyl-2'-phenyl-2H,2'H-[3,4']bipyrazolyl-3'-ol, and 2,5,5'-Trimethyl-2'-phenyl-2H,2'H-[3,4']bipyrazolyl-3'-ol.

In yet another embodiment of the compound of formula I of this invention, $R_1$ is aryl, $R_2$ and $R_3$ are $C_{1-6}$alkyl, $R_4$ is aryl, and $R_5$ is hydrogen.

Representative examples of compounds of this embodiment of the compound of formula I are selected from the group consisting of: 2-(4-Methoxy-phenyl)-5,5'-dimethyl-2'-phenyl-2H,2'H-[3,4']bipyrazolyl-3'-ol and 2-(4-Fluoro-phenyl)-5,5'-dimethyl-2'-phenyl-2H,2'H-[3,4']bipyrazolyl-3'-ol.

In another embodiment of the compound of formula I of this invention, $R_1$ is aryl$C_{2-6}$alkyl or benzyl, $R_2$ and $R_3$ are $C_{1-6}$alkyl, and $R_4$ and $R_5$ are hydrogen.

Representative examples of compounds of this embodiment of the compound of formula I are selected from the group consisting of: 5,5'-Dimethyl-2'-phenethyl-2H,2'H-[3,4']bipyrazolyl-3'-ol, 2'-(3-Hydroxy-benzyl)-5,5'-dimethyl-2H,2'H-[3,4']bipyrazolyl-3'-ol, and 2'-Benzyl-5,5'-dimethyl-2H,2'H-[3,4']bipyrazolyl-3'-ol.

In a further embodiment of the compound of formula I of this invention, $R_1$ is

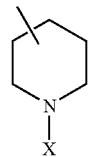

wherein X is benzyl, $R_2$ and $R_3$ are $C_{1-6}$alkyl, and $R_4$ and $R_5$ are hydrogen.

A compound exemplary of this embodiment of the compound of formula I is 2'-(1-Benzyl-piperidin-4-yl)-5,5'-dimethyl-2H,2'H-[3,4']bipyrazolyl-3'-ol.

In another embodiment of the compound of formula I of this invention, $R_1$ is $C_{3-8}$cycloalkyl, $R_2$ and $R_3$ are $C_{1-6}$alkyl, and $R_4$ and $R_5$ are hydrogen.

A compound exemplary of this embodiment of the compound of formula I is 2'-Cyclohexyl-5,5'-dimethyl-2H-2'H-[3,4]bipyrazolyl-3'-ol.

In another embodiment of this invention is disclosed a compound which is 5,1',5'-trimethyl-2'-phenyl-1',2'-dihydro-2H-[3,4']bipyrazolyl-3'-one.

In another embodiment of the present invention is disclosed a pharmaceutical composition comprising an effective amount of a compound of formula I and a pharmaceutically acceptable carrier.

In still another embodiment of the present invention, is disclosed a method of treating a neuropsychiatric disorder responsive to modulation of AMPA and NMDA receptors, comprising administering to a mammal in need of said treatment a therapeutically effective amount of a compound of formula I

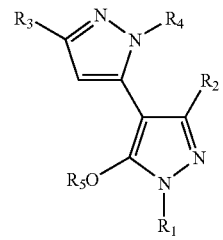

or a stereoisomer or pharmaceutically acceptable salt thereof, wherein:

$R_1$ is selected from the group consisting of aryl, benzyl, $C_{3-8}$cycloalkyl, $C_{1-10}$alkyl, $C_{3-8}$cycloalkyl$C_{1-6}$alkyl, hetero-aryl, arylcarbonyl, aryl$C_{1-6}$alkyl$C_{3-8}$cycloalkylcarbonyl, $C_{1-10}$alkylcarbonyl, hetero-arylcarbonyl and

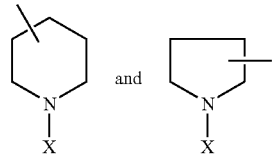

wherein X is hydrogen, benzyl, aryl$C_{2-6}$alkyl, $C_{3-8}$cycloalkyl, $C_{1-10}$alkyl, or $C_{3-8}$cycloalkyl$C_{1-6}$alkyl;

wherein said aryl, benzyl, or hetero-aryl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, or aryl;

$R_2$ is selected from the group consisting of $C_{1-6}$alkyl, $C_{3-8}$cycloalkyl, and aryl wherein said aryl is optionally substituted with one or more substituents each independently selected from $C_{1-6}$alkyl, $C_{1-6}$ perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy;

$R_3$ is selected form the group consisting of aryl, $C_{3-8}$cycloalkyl, $C_{1-6}$alkyl and hetero-aryl wherein said aryl or hetero-aryl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy;

$R_4$ is selected form the group consisting of H, aryl, aryl$C_{2-6}$alkyl, benzyl, hydroxy$C_{2-6}$alkyl $C_{1-6}$perfluoroalkyl, $C_{3-8}$cycloalkyl and $C_{1-6}$alkyl wherein said aryl or benzyl is optionally substituted with one or more substituents each independently selected from $C_{1-6}$alkyl, $C_{1-6}$perfluoroalkyl, halogen, hydroxy, $C_nH_xF_{y-6}$alkoxy wherein n is 1-4, x is 0-8, y is 1-9 and x+y is 2n+1, $C_1$-$C_6$alkoxy, nitro, aryl, or alkoxy; and $R_5$ is H, $C_{1-6}$alkyl, or $C_{3-8}$cycloalkyl.

In another embodiment of the method of this invention, said neuropsychiatric disorder is selected from the group consisting of depression, epilepsy, schizophrenia, Alzheimer's, disease, learning and memory disorders; and mild cognitive impairment.

In a further embodiment of the method of this invention, said disorder is schizophrenia.

In yet another embodiment of the method of this invention, said disorder is depression.

In still another embodiment of the method of this invention, said disorder is learning and memory disorder.

The compounds of the invention may be prepared by the synthetic routes described below in the Schemes or by other methods, which may be apparent to those skilled in the art The R substituents are as identified for formula (I), above unless otherwise noted. If necessary, in the following synthetic schemes, reactive functional groups present in the compounds described in this invention may be protected by suitable protecting groups. The protecting group may be removed at a later stage of the synthesis. Procedures for protecting reactive functional groups and their subsequent removal may be found in T. W. Greene and P. G. M. Wuts, *Protective Groups in Organic Synthesis*, Wiley and Sons, 1991.

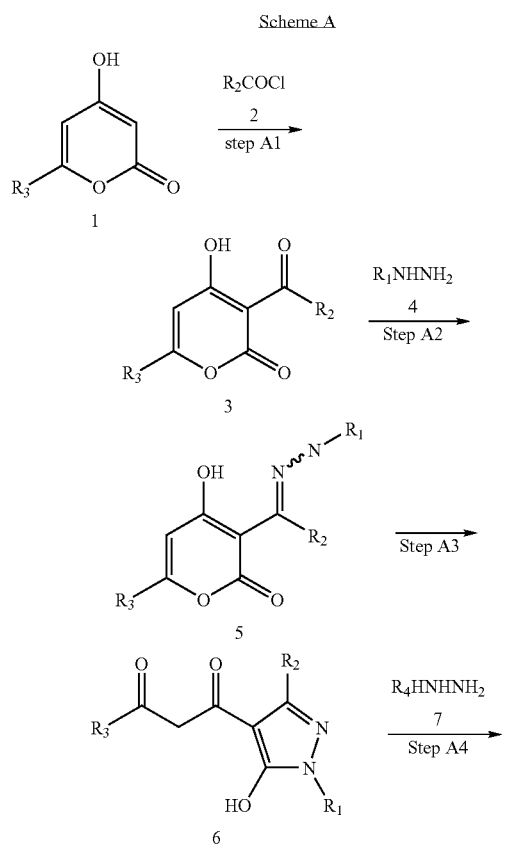

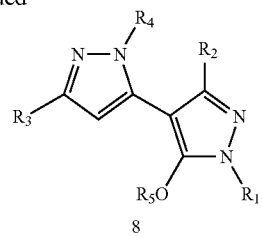

Scheme A shows the synthesis of a compound of formula I wherein $R_4$ and $R_5$ are hydrogen. In Step A1, the 6-substituted pyrone 1, a compound which is either commercially available or can readily be synthesized by methods well known in the art (Lokot, et al, *Tetrahedron*, 55, 4783-4792, 1999), is reacted with a carboxylic acid chloride, compound 2, in the presence of a strong organic acid, to give the 3-acylated derivative 3. Suitable strong organic acids that may be used in the reaction are for example, a trihaloacetic acid such as trifluoroacetic acid or a trifluoroalkylsulfonic acid. The reaction is typically run at temperatures of from 50° C. to the reflux temperature of the acid.

In Step A2, compound 3 is reacted with a hydrazine 4 to form the hydrazone, compound 5. The reaction is typically performed in an inert organic solvent such as an alcohol, optionally in the presence of a suitable base if a hydrazine salt is used as a reactant. Suitable alcohols include methanol, ethanol, isopropanol or ethylene glycol and suitable bases include alkali carbonates such as sodium, potassium or cesium carbonates, or resin bound carbonates such as MP-carbonate. The temperature at which the reaction can be run is from ambient to the reflux temperature of the organic solvent.

As shown in Step A3 the hydrazone, compound 5, can be converted to the pyrazolyl dione 6 by affecting an intramolecular cyclization of 5 in the presence of a suitable organic acid such as acetic, propionic or trifluoroacetic acid. The reaction is typically run at elevated temperatures from about 50° C. to the reflux temperature of the organic acid.

In Step A4, reaction of the dione 6 with hydrazine 7 gives the desired bipyrazole 8. The reaction is typically run in an inert organic solvent such as an alcohol at or near the reflux temperature of the solvent.

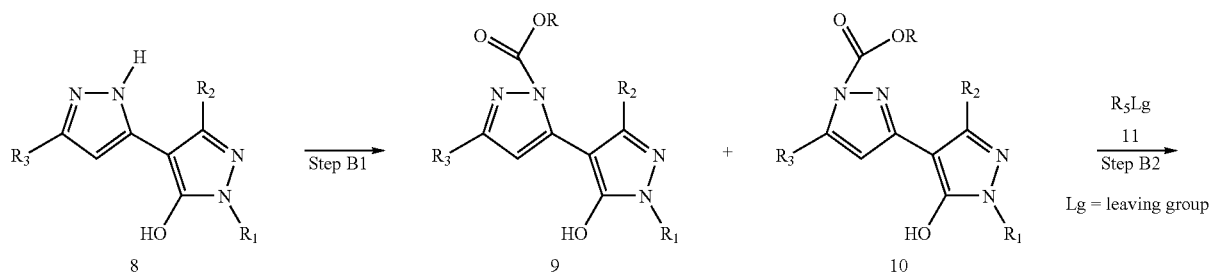

-continued

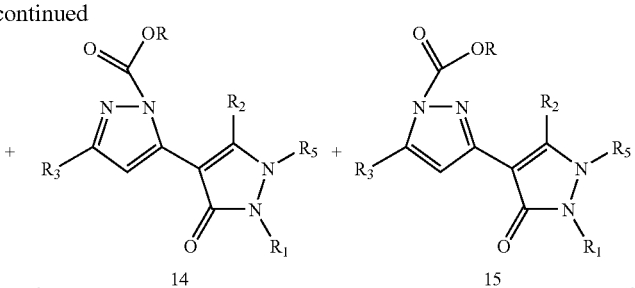

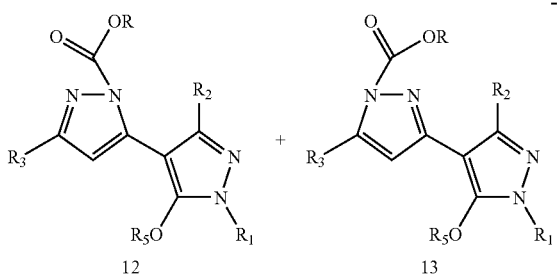

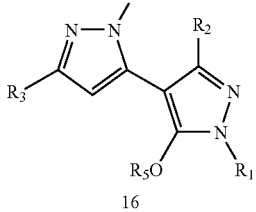

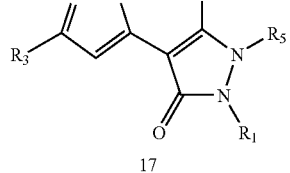

Scheme B illustrates a method that can be used to synthesize compounds of formula I wherein and $R_5$ is $C_{1-6}$alkyl, $C_{3-8}$cycloalkyl. In Step B1 the unsubstituted ring nitrogen of the bipyrazole 8 is protected with an alkoxycarbonyl group to give a mixture of positional isomers, compounds 9 and 10. The reaction is accomplished by using methods well known in the art for instance treatment of 8 with t-butylcarbazate can give compound 9. See Kashuma, et al, *Tetrahedron*, 54, 14679, 1998.

In Step B2 the mixture of isomers 9 and 10 are reacted with an alkylating/cycloalkylating agent 11 wherein Lg is a leaving group such as halogen, alkylsulfonate or arylsulfonate to produce a mixture of the O-alkylated compounds 12 and 13 and the N-alkylated compounds 14 and 15. The reaction can be run in a polar aprotic solvent such as DMF, DMSO or acetonitrile in the presence of a suitable base. Suitable bases include the alkaline and alkali carbonates and bicarbonates such as potassium and sodium carbonate and bicarbonate. The temperature at which the reaction can be run is from ambient to the reflux temperature of the organic solvent. Following workup of the reaction, chromatography on silica gel gives two separate mixtures. One mixture consists of the O-alkylated compounds 12 and 13 the other consists of N-alkylated compounds 14 and 15.

The O-alkylated target compound 16 can be obtained as depicted in Step B3 by cleavage of the N-alkoxycarbonyl from the positional isomers 12 and 13. The cleavage can be accomplished by methods that are well known in the art, for example by acid or base treatment of 12 and 13.

Similarly, Step B4 employs identical conditions as Step B3 to give the N-alkylated compound 17.

BIOLOGICAL EXAMPLES

The following test protocols are used to ascertain the biological properties of the compounds of this invention. The following examples are being presented to further illustrate the invention. However, they should not be construed as limiting the invention in any manner.

Spinophilin/Protein Phosphatase-1 Interaction Assay:
Materials:
10× stock TBS (Tris-Buffered Saline) is from Bio-Rad. Spinophilin (6×His) and GST-PP1 proteins are cloned, expressed, and purified in house by protein production. Eu-anti-GST antibody, DELFIA assay buffer and DELFIA Enhancement solution are from Wallac (now Perkin Elmer). High binding 384 well plates are from Greiner.

Methods for ELISA Time-Resolved Fluorescence 384-Well Assay:
Plates are coated with 50 ul of Spinophilin/TBS solution (50 ug/ml) or 50 ul of TBS buffer (0 control) and incubated overnight @ 4° C. Test compounds are prepared and diluted in 96-well polypropylene plates using a Labsystems Wellpro Liquid Handler. After washing the plates 3 times with TBS using the Elx-405 (Biotek) plate washer, the compounds are transferred from the 96-well plate to the 384-well plate using a Multimek (Beckman) liquid handler. GST-PP1, 50 ul (2.5 ug/ml) is then added to the plate. Plates are incubated for 3-6 h @ room temperature. The plates are washed 3 times as above and 50 ul of Eu-anti-GST antibody (~50 ng/ml) are added using a Multidrop (Titertek) module and allowed to incubate for 30 min at room temperature. The plates are washed 3 times as above and 100 ul of Enhancement Solution are added with the Multidrop module and allowed to incubate for 1 h @ room temperature. Plates are read in the Farcyte (Tecan) Fluorescence reader using Europium setting. Compounds are evaluated for their ability to inhibit the interaction of Spinophilin (6×His) and GST-PP1 by measuring a reduction in the fluorescence signal.

Voltage Whole-Cell Recording of AMPA and NMDA Currents in Prefrontal Cortical Neurons:
Neuronal Acute-Dissociation Method:
Prefrontal cortical (PFC) neurons from young adult (3-5 weeks postnatal) rats are acutely dissociated using procedures similar to those described previously (Feng, et al., J Neurosci, 2001; Chen, et al., Proc Natl Acad Sci USA, 2004). After incubation of brain slices in a NaHCO$_3$-buffered saline, PFC is dissected and placed in an oxygenated chamber containing papain (Sigma, 0.8 mg/ml) in HEPES-buffered Hank's balanced salt solution (HBSS, Sigma) at room temperature. After 40 minutes of enzyme digestion, tissue is rinsed three times in the low $Ca^{+2}$, HEPES-buffered saline and mechanically dissociated with a graded series of fire-polished Pasteur pipettes. The cell suspension is then plated into a 35 mm Lux Petri dish, which is then placed on the stage of a Nikon inverted microscope.

Whole-Cell Recording of AMPA and NMDA:

Whole-cell recordings of whole-cell ion channel currents employ standard voltage clamp techniques (Yan et al., *Nat Neuroscience*, 1999; Wang et al., *J Neurosci*, 2003; Tyszkiewicz et al., *J. Physiol.*, 2004). The internal solution (inside the patch pipette) consists of (in mM): 180 N-methyl-d-glucamine (NMG), 40 HEPES, 4 $MgCl_2$, 0.1 BAPTA, 12 phosphocreatine, 3 $Na_2ATP$, 0.5 $Na_2GTP$, 0.1 leupeptin, pH=7.2-7.3, 265-270 mosm/L. The external solution consists of (in mM): 127 NaCl, 20 CsCl, 10 HEPES, 1 $CaCl_2$, 5 $BaCl_2$, 12 glucose, 0.001 TTX, 0.02 glycine, pH=7.3-7.4, 300-305 mOsm/L. Recordings are obtained with an Axon Instruments 200B patch clamp amplifier that is controlled and monitored with an IBM PC running pCLAMP (v. 8) with a DigiData 1320 series interface (Axon instruments). Electrode resistances are typically 2-4 MΩ in the bath. After seal rupture to attain whole-cell recording conditions, series resistance (4-10 MΩ) is compensated (70-90%) and periodically monitored. The cell membrane potential is held at −60 mV.

The application of KA (200 µM) or NMDA (100 µM, in $Mg^{2+}$-free solution) evokes a partially desensitizing inward current. KA or NMDA is applied for 2 seconds every 30 seconds to minimize desensitization-induced decrease of current amplitude. Drugs are applied with a gravity-fed 'sewer pipe' system. The array of application capillaries (ca. 150 µm i.d.) is positioned a few hundred microns from the cell under study. Solution changes are effected by the SF-77B fast-step solution stimulus delivery device (Warner Instruments). Data are collected with PCLAMP software and analyzed with AXOGRAPH, KALEIDOGRAPH, and STATVIEW.

Compounds described herein inhibit the KA-induced rundown of AMPA current by either stabilizing the agonist-evoked current of increasing the current. Likewise, compounds described herein increase the NMDA-evoked current. The minimum effective dose (MED) was identified by determining the lowest concentration of inhibitor that was effective in each functional assay.

The results of these assays are shown in Table I and Table II.

TABLE I

Inhibition of KA-Induced Rundown of AMPA Current

| Example No. | Minimal Effective Concentration (µM) |
| --- | --- |
| 4 | 0.1 * |
| 5 | 0.1 * |
| 15 | 1.0 |
| 18 | 1.0 |
| 25 | 1.0 |

* Lowest concentration tested (MED possibly less than 100 nM).

TABLE II

Increase of NMDA-Evoked Current

| EXAMPLE # | Minimal Effective Concentration (µM) | Average percent increase in NMDA current (10 µM) |
| --- | --- | --- |
| 8 | 1 | 303% (n = 3 neurons) |
| 18 | 5 | 55% (n = 4 neurons) |

Porsolt's Forced Swim Test:

The effects measured in this model have been correlated to antidepressant efficacy for drugs. The paradigm of this model is that an effective antidepressant compound will cause a rat to make greater attempts to escape a water-filled cylinder than a rat given vehicle only.

Animals used in this study are non-naive male Sprague Dawley rats weighing between 225-350 grams. The test apparatus consists of 6 clear PLEXIGLAS® cylinders 40 cm high×19 cm wide. Cylinders are filled to 18 cm with 25° C. water. Each rat is placed in a cylinder for a 15-minute training session. Following either subchronic or acute dosing of either vehicle (0.5% methylcellulose) or compound, animals are brought back 24 hours later for a 5-minute test session. These test sessions are videotaped for later scoring.

Subchronic dosing consists of administering drug three times in the 24-hour period between training and testing. The drug is administered 24 hrs., 5 hrs., and 1 hr. prior to the test session. Acute dosing consists of administering the drug once, 1 hour prior to the test session. Scoring is done using a time-sampling computer program. Every five seconds, animals are rated as demonstrating one of three behaviors: immobility, mild swim, or climbing. These sampling scores are then converted into percentages of the test session.

It will be appreciated that every suitable combination of the compounds of the invention with one or more of the aforementioned compounds and optionally one or more other pharmacologically active substances is regarded as falling within the scope of the claims of the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

Object Recognition Test:

The object recognition test is a memory test. It measures the ability of mice (and rats) to differentiate between known and unknown objects and is therefore suitable for the determination of the memory-improving action of the compounds according to the invention.

The test can generally be carried out as described in the literature. (Blokland et al. *NeuroReport* 1998, 9, 4205-4208; Ennaceur, A., Delacour, J., *Behav. Brain Res.* 1988, 31, 47-59; Ennaceur, A., Meliani, K., *Psychopharmacology* 1992, 109, 321-330; Prickaerts, et al. *Eur. J. Pharmacol.* 1997, 337, 125-136).

In a first passage, a mouse in an otherwise empty, relatively large observation arena is confronted with two identical objects. The mouse will extensively examine, i.e. sniff and touch, both objects. The amount of time the mouse spends with each object is scored. In a second passage, after an interval of 24 hours, the mouse is again tested in the observation arena. One of the known objects is now replaced by a new, unknown object. When a mouse recognizes the known object, it will especially examine the unknown object. After 24 hours, a mouse, however, has normally forgotten which object it has already examined in the first passage, and will therefore inspect both objects equally intensively. The administration of a substance having learning- and memory-improving action will lead to a mouse recognizing the object already seen 24 hours beforehand, in the first passage, as known. It will examine the new, unknown object in greater detail than the already known one. This memory power is expressed in a discrimination index. A discrimination index of zero means that the mouse examines both objects, the old and the new one, for the same length of time; i.e. it has not recognized the old object and reacts to both objects as if they are both unknown and new. A discrimination index of greater than zero means that the mouse has inspected the new object for longer than the old one; i.e. the mouse has recognized the old object.

MK-801-Induced Psychosis Model:

The non-competitive NMDA receptor antagonist MK-801 induces stereotypies and hyperactivity in rodents (Contreras et al., *Synapse* 2: 240-243, 1988) by interacting with the NMDA receptor-associated ion channel. Phencyclidine, which also interferes with the NMDA receptor, produces psychotic effects in humans similar in many respects to schizophrenia. These findings suggest that a deficiency in glutamate transmission may be responsible in the pathology of schizophrenia (Javitt & Zukin, *Am. J. Psychiatr.*, 48:1301-1308, 1991). The neuroleptics haloperidol, clozapine and raclopride are able to reverse the behavioral changes induced by MK-801 in rats (Carlsson et al., *Biol. Psychiatr.* 46: 1388-1395, 1999). Therefore the MK-801-induced activity and stereotypies in rats may represent an appropriate animal model to test the potential efficacy of antipsychotic drugs.

Experimental Procedures

Male Wistar rats, weight 250-300 g are housed 2 per cage on a 12 h/12 h light dark cycle (lights on at 7.00 a.m.) at a room temperature of 21.+-0.2.degree. C. for a minimum of 5 days before testing. All animals are given access to commercial food and tap water ad libitum.

On the day of the experiment, rats are treated with reference drug vehicle, the reference drugs haloperidol or clozapine, the test compound vehicle, or test compounds. After administration, the rats are returned to their home cages for 15 minutes. The haloperidol, clozapine, test compound and vehicle treated animals receive an i.p. injection of 0.3 mg/kg MK-801. The remaining rats treated with placebo receive a second injection of vehicle. The standard injection volume is 2.0 ml/kg. After 10 minutes in the home cages, rats are transferred to the test box (Plexiglas, 29.times.12.times.12 cm), 5 minutes before the assessment for accommodation. The test box is cleaned with 70% ethanol before each assessment. Stereotypies, defined as wall-contacts with the snout, and locomotion, defined as turn-rounds of 180.degree., are assessed during 5 minute periods.

Metrazole Potentiation Assay

Male CD-1 mice (20-30 grams) are used. On the day of testing, animals are brought to the laboratory and randomly assigned to groups. For a primary screen, the test compound is administered intraperitoneally (i.p., 10 ml/kg) to groups of 10 mice 60 minutes prior to challenge with metrazol (55 mg/kg sc). Post-metrazol administration animals are placed individually into clear plastic cylinders (12×5 inches) and then observed for clonic seizures. A clonic seizure is defined as a single episode of clonic spasms of at least 3-second duration. The mice treated with metrazol are considered "potentiated" when these clonic seizures occur.

A dose range is necessary when 50% of the animals demonstrate potentiation in the primary screen. Test compounds are tested at the 60-minute pretreatment time using 3 or more doses with a vehicle control group. The ED50 value is determined by linear regression.

$$\frac{\% \, Rx \text{ group} - \% \text{ vehicle group}}{100 - \% \text{ vehicle group}}$$

Supramaximal Electroshock Assay

Male CD-1 mice (18-30 g) are used. Drugs are prepared using distilled water and if insoluble a surfactant is added. Control animals receive vehicle. Drugs are routinely administered intraperitoneally. The route of administration may be varied (p.o., s.c.). The dosage volume is 10 ml/kg.

A constant current stimulator, similar to the apparatus described by Woodbury and Davenport (*Arch. Int. Pharmacodyn.* 92: 97-107, 1952) delivers a 60 Hz shock of variable current and duration through corneal electrodes. A 0.3 s, 25 mA shock (50V) is sufficient to produce extensor tonus in 95% of control mice.

A compound is considered to give protection if the mouse does not exhibit extensor tonus. Protection is expressed as normalized percent inhibition relative to vehicle control. A time response is carried out using 6 animals per group. Animals are tested at 30, 60, and 120 min post-drug. Additional time periods are tested if indicated by previous tests. When peak activity has been determined, a dose-response is initiated, using 10 animals per group at that time period. The ED50 and 95% confidence interval are calculated by computerized probit analysis.

SYNTHETIC EXAMPLES

General

Commercial reagents and solvents are used as received. $^1$H NMR spectra are recorded on a Varian MercuryPlus-300 (300 MHz) or Varian Unity Inova (400 MHz) spectrometer as indicated. Proton chemical shifts are reported in ☐ ppm relative to internal tetramethylsilane (0.0 ppm). MS (LC-MS) data is obtained using a Micromass LCT time of flight mass spectrometer with electrospray ionization and 5 min data acquisition time for m/z 100 to 1000. LC (LC-MS) is performed using a Hypersil C18 column (4.6×50 mm, 3.5☐ with mobile phase of 0.1% TFA in $H_2O$ (A) and 0.1% TFA in ACN (B) and a gradient of 5% to 100% B over 3 min followed by 2 min at 100% B. Alternatively, a Platform LC-MS with electrospray source may be used with a HP1100 LC system running at 2.0 ml/min, 200 □L/min split to the ESI source with inline HP1100 DAD detection and SEDEX ELS detection. A Luna C18(2) column (30×4.6 mm 3□ is used with a gradient of 5% to 95% B over 4.5 min with mobile phase of 0.1% formic acid in H₂O and 0.1% formic acid in ACN (B). HPLC purification is performed on a Varian ProStar system using a reversed-phase C18 column with a linear gradient of ACN/H₂O containing 0.1% trifluoroacetic acid.

Example 1

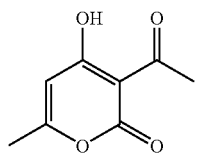

3-Acetyl-4-hydroxy-6-methyl-pyran-2-one

Dissolve 4-hydroxy-6-methyl-pyran-2-one (12.6 g, 100 mmol) in trifluoroacetic acid (50 ml). and add 7.8 g (100 mml) of acetyl chloride dropwise. Heat this mixture at reflux for 5 hours. Evaporate the reaction mixture under reduced pressure. Add 50 ml of water, extract with ethyl acetate (50 ml×3) and combine the organic layers. Wash with brine and dry (sodium sulfate). Chromatograph on silica gel, eluting with chloroform to provide 5.8 g (34.5 mmol) of 3-acetyl-4-hydroxy-6-methyl-pyran-2-one.

LCMS (M+H): m/z 169, retention time 3.24 min.

Example 2

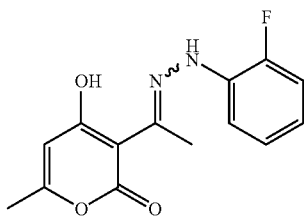

3-{1-[(2-Fluoro-phenyl)-hydrazono]-ethyl}-4-hydroxy-6-methyl-pyran-2-one

To 2-fluorophenyl hydrazine hydrochloride (0.16 g, 1.0 mmol) in methanol (8 ml) add MP-carbonate (1.0 g, 3.3 equivalents). Shake this mixture at room temperature for 1 hour. Filter the resin and wash with methanol. To the filtrate add (2-fluorophenyl)-hydrazine (0.134 g, 0.80 mmol). Shake the reaction mixture at room temperature for 2 hours after which evaporate the solvent under reduced pressure. Recrystallize the solid from a minimum amount of methanol and obtain 0.185 g (0.67 mmol) of 3-{1-[(2-fluoro-phenyl)-hydrazono]-ethyl}-4-hydroxy-6-methyl-pyran-2-one.

LCMS (M+H): m/z 277, retention time 2.74 min.

Example 3

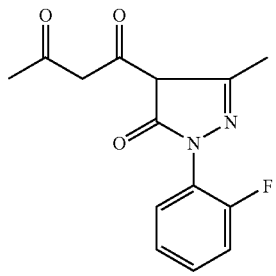

1-[1-(2-Fluoro-phenyl)-3-methyl-5-oxo-4,5-dihydro-1H-pyrazol-4-yl]-butane-1,3-dione Heat at reflux for 1 hour 3-{1-[(2-fluoro-phenyl)-hydrazono]-ethyl}-4-hydroxy-6-methyl-pyran-2-one (0.045 g, 0.163 mmol) in acetic acid (0.3 ml). Add heptane (3 ml) and evaporate the mixture to dryness to give 1-[1-(2-fluoro-phenyl)-3-methyl-5-oxo-4,5-dihydro-1H-pyrazol-4-yl]-butane-1,3-dione (0.045 g, 0.163 mmol). Use this material for the next step without further purification.

LCMS (M+H): m/z 277, retention time 2.05 min.

Example 4

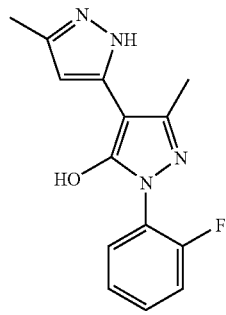

2'-(2-Fluoro-phenyl)-5,5'-dimethyl-2H,2'H-[3,4']bipyrazolyl-3'-ol

Add to 1-[1-(2-fluoro-phenyl)-3-methyl-5-oxo-4,5-dihydro-1H-pyrazol-4-yl]-butane-1,3-dione (0.045 g, 0.163 mmol) hydrazine hydrate (0.016 g, 0.32 mmol) in ethanol (1.6 ml). Heat the reaction mixture at reflux for 1.5 hours after which evaporate the ethanol. Wash the residue with dichloromethane to give 2'-(2-fluoroxphenyl)-5,5'-dimethyl-2H, 2'H-[3,4']bipyrazolyl-3'-ol (0.028 g, 0.102 mmol).

LCMS (M+H): m/z 273, retention time 2.16 min.

Example 5

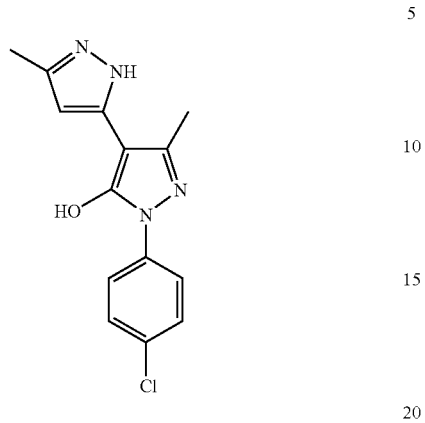

2'-(4-Chloro-phenyl)-5,5'-dimethyl-2H,2'H-[3,4']bipyrazolyl-3'-ol

Prepare the title compound from 3-acetyl-4-hydroxy-6-methyl-pyran-2-one and 4-chlorophenyl hydrazine hydrochloride according to the procedure illustrated in Examples 2, 3 and 4.

LCMS (M+H): m/z 289, retention time 2.72 min.

Example 6

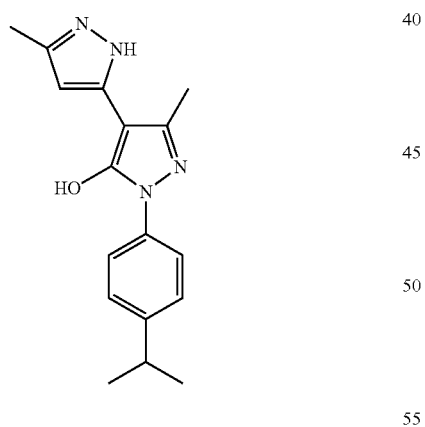

2'-(4-Isopropyl-phenyl)-5,5'-dimethyl-2H,2'H-[3,4']bipyrazolyl-3'-ol

Prepare the title compound from 3-acetyl-4-hydroxy-6-methyl-pyran-2-one and 4-isopropylphenylhydrazine hydrochloride according to the procedure illustrated in Examples 2, 3 and 4.

LCMS (M+H): m/z 297, retention time 2.85 min.

Example 7

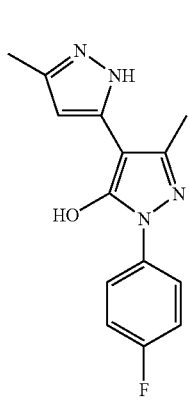

2'-(4-Fluoro-phenyl)-5,5'-dimethyl-2H,2'H-[3,4']bipyrazolyl-3'-ol

Prepare the title compound from 3-acetyl-4-hydroxy-6-methyl-pyran-2-one and 4-fluorophenyl hydrazine hydrochloride according to the procedure illustrated in Examples 2, 3 and 4.

LCMS (M+H): m/z 273, retention time 2.00 min.

Example 8

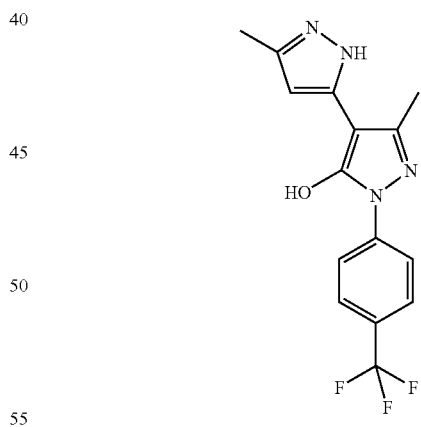

5,5'-Dimethyl-2'-(4-trifluoromethyl-phenyl)-2H,2'H-[3,4']bipyrazolyl-3'-ol

Prepare the title compound from 3-acetyl-4-hydroxy-6-methyl-pyran-2-one and 4-trifluoromethylphenyl hydrazine according to the procedure illustrated in Examples 2, 3 and 4.

LCMS (M+H): m/z 323, retention time 2.88 min.

Example 9

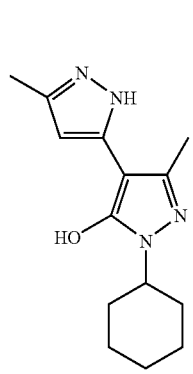

2'-Cyclohexyl-5,5'-dimethyl-2H, 2'H-[3,4]bipyrazolyl-3'-ol

Prepare the title compound from 3-acetyl-4-hydroxy-6-methyl-pyran-2-one and cyclohexylhydrazine hydrochloride according to the procedure illustrated in Examples 2, 3 and 4.
LCMS (M+H): m/z 261, retention time 1.80 min.

Example 10

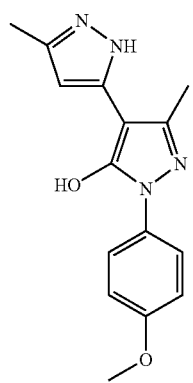

5,5'-Dimethyl-2'-(4-methoxy-phenyl)-2H,2'H-[3,4']bipyrazolyl-3'-ol

Prepare the title compound from 3-acetyl-4-hydroxy-6-methyl-pyran-2-one and 4-methoxyphenyl hydrazine hydrochloride according to the procedure illustrated in Examples 2, 3 and 4.
LCMS (M+H): m/z 285, retention time 1.96 min.

Example 11

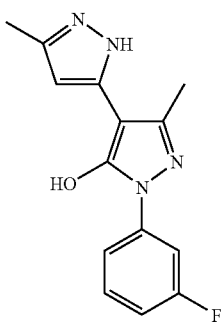

2'-(3-Fluoro-phenyl)-5,5'-dimethyl-2H,2'H-[3,4'] bipyrazolyl-3'-ol

Prepare the title compound from 3-acetyl-4-hydroxy-6-methyl-pyran-2-one and 3-fluorophenyl hydrazine hydrochloride according to the procedure illustrated in Examples 2, 3 and 4.
LCMS (M+H): m/z 273, retention time 2.45 min.

Example 12

2'-(2-Methyl-phenyl)-5,5'-dimethyl-2H,2'H-[3,4'] bipyrazolyl-3'-ol

Prepare the title compound from 3-acetyl-4-hydroxy-6-methyl-pyran-2-one and 2-methylphenyl hydrazine hydrochloride according to the procedure illustrated in Examples 2, 3 and 4.
LCMS (M+H): m/z 269, retention time 1.70 min.

Example 13

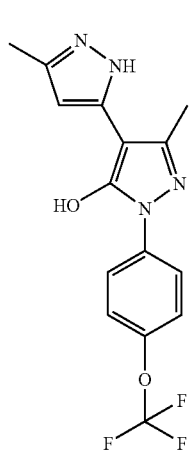

5,5'-Dimethyl-2'-(4-trifluoromethoxy-phenyl)-2H,2'H-[3,4']bipyrazolyl-3'-ol

Prepare the title compound from 3-acetyl-4-hydroxy-6-methyl-pyran-2-one and 4-trifluoromethoxyphenyl hydrazine hydrochloride according to the procedure illustrated in Examples 2, 3 and 4.

LCMS (M+H): m/z 339, retention time 3.02 min.

Example 14

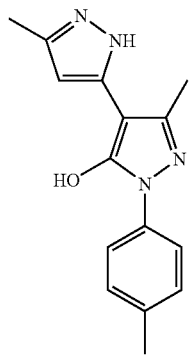

5,5'-Dimethyl-2'-(4-methyl-phenyl)-2H,2'H-[3,4']bipyrazolyl-3'-ol

Prepare the title compound from 3-acetyl-4-hydroxy-6-methyl-pyran-2-one and 4-methyl-phenyl hydrazine hydrochloride according to the illustrated in Examples 2, 3 and 4.

LCMS (M+H): m/z 269, retention time 2.44 min.

Example 15

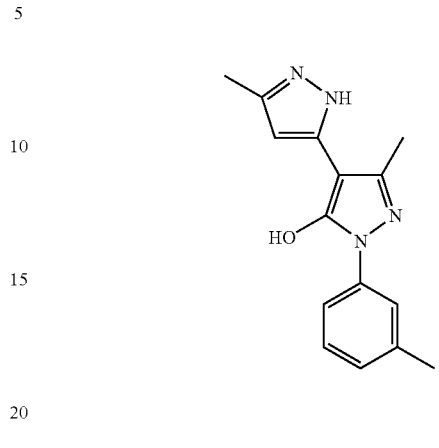

5,5'-Dimethyl-2'-(3-methyl-phenyl)-2H,2'H-[3,4']bipyrazolyl-3'-ol

Prepare the title compound from 3-acetyl-4-hydroxy-6-methyl-pyran-2-one and 3-methylphenyl hydrazine hydrochloride according to the procedure illustrated in Examples 2, 3 and 4.

LCMS (M+H): m/z 269, retention time 2.46 min.

Example 16

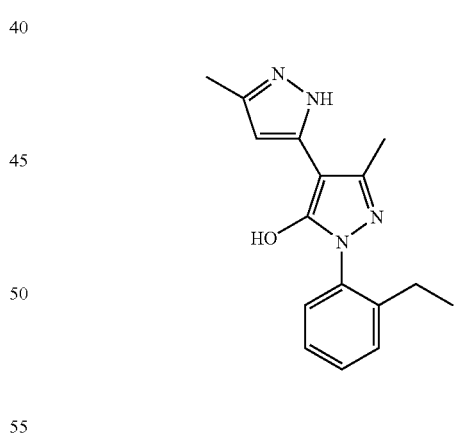

5,5'-Dimethyl-2'-(2-ethyl-phenyl)-2H,2'H-[3,4']bipyrazolyl-3'-ol

Prepare the title compound from 3-acetyl-4-hydroxy-6-methyl-pyran-2-one and 2-ethylphenylhydrazine hydrochloride according to the procedure illustrated in Examples 2, 3 and 4.

LCMS (M+H): m/z 283, retention time 2.32 min.

Example 17

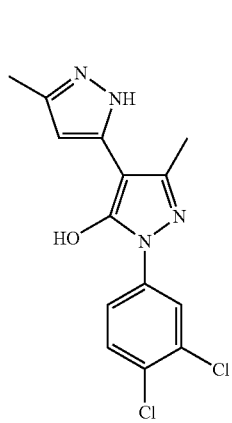

5,5'-Dimethyl-2'-(3,4-dichloro-phenyl)-2H,2'H-[3,4']bipyrazolyl-3'-ol

Prepare the title compound from 3-acetyl-4-hydroxy-6-methyl-pyran-2-one and 3,4-dichlorophenyl hydrazine hydrochloride according to the procedure illustrated in Examples 2, 3 and 4.

LCMS (M+H): m/z 323, retention time 3.04 min.

Example 18

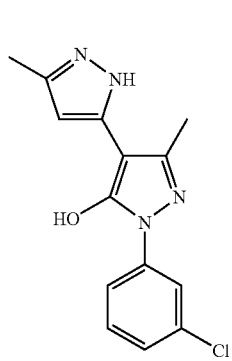

5,5'-Dimethyl-2'-(3-chlorophenyl)-2H,2'H-[3,4']bipyrazolyl-3'-ol

Prepare the title compound from 3-acetyl-4-hydroxy-6-methyl-pyran-2-one and 3-chlorophenyl hydrazine hydrochloride according to the procedure illustrated in Examples 2, 3 and 4.

LCMS (M+H): m/z 289, retention time 2.28 min.

Example 19

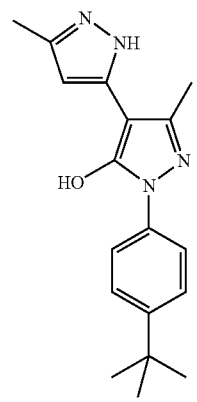

2'-(4-tert-Butyl-phenyl)-5,5'-dimethyl-2H,2'H-[3,4']bipyrazolyl-3'-ol

Prepare the title compound from 3-acetyl-4-hydroxy-6-methyl-pyran-2-one and 4-tert-butylphenylhydrazine hydrochloride according to the procedure illustrated in Examples 2, 3 and 4.

LCMS (M+H): m/z 311, retention time 2.62 min.

Example 20

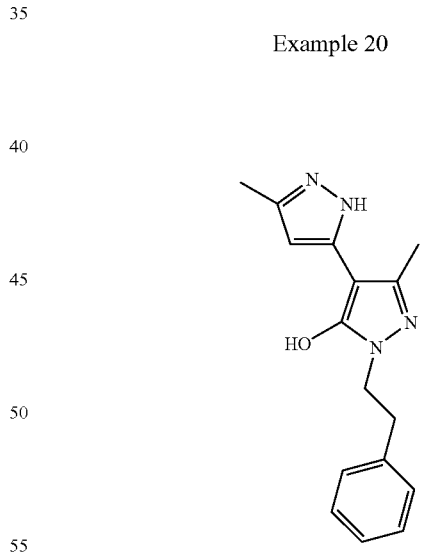

5,5'-Dimethyl-2'-phenethyl-2H,2'H-[3,4']bipyrazolyl-3'-ol

Prepare the title compound from 3-acetyl-4-hydroxy-6-methyl-pyran-2-one and phenethylhydrazine sulfate according to the procedure illustrated in Examples 2, 3 and 4.

LCMS (M+H): m/z 283, retention time 2.07 min.

Example 21

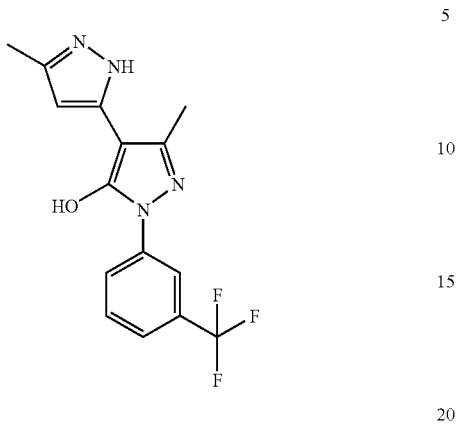

5,5'-Dimethyl-2'-(3-trifluoromethyl-phenyl)-2H,2'H-[3,4']bipyrazolyl-3'-ol

Prepare the title compound from 3-acetyl-4-hydroxy-6-methyl-pyran-2-one and 3-trifluoromethylphenyl hydrazine hydrochloride according to the procedure illustrated in Examples 2, 3 and 4.

LCMS (M+H): m/z 323, retention time 2.62 min.

Example 22

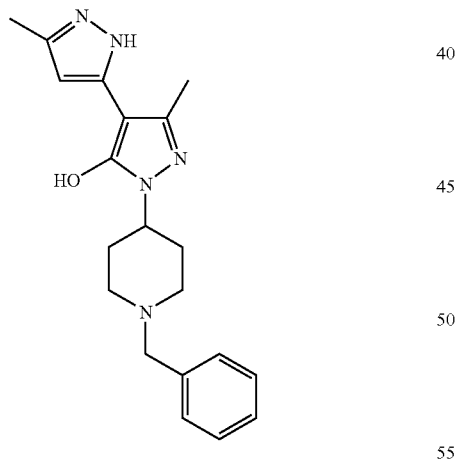

2'-(1-Benzyl-piperidin-4-yl)-5,5'-dimethyl-2H,2'H-[3,4']bipyrazolyl-3'-ol

Prepare the title compound from 3-acetyl-4-hydroxy-6-methyl-pyran-2-one and 1-benzylpiperidin-4-yl hydrazine dihydrochloride according to the procedure illustrated in Examples 2, 3 and 4.

LCMS (M+H): m/z 352, retention time 1.52 min.

Example 23

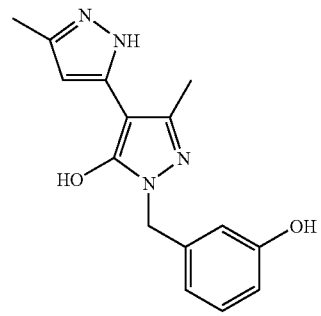

2'-(3-Hydroxy-benzyl)-5,5'-dimethyl-2H,2'H-[3,4']bipyrazolyl-3'-ol

Prepare the title compound from 3-acetyl-4-hydroxy-6-methyl-pyran-2-one and 3-hydrazinomethylphenol dihydrochloride according to the procedure illustrated in Examples 2, 3 and 4.

LCMS (M+H): m/z 285, retention time 1.57 min.

Example 24

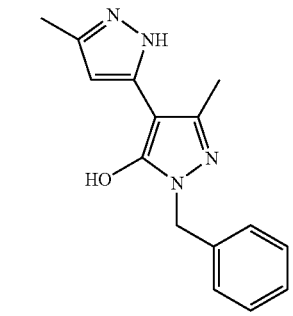

2'-Benzyl-5,5'-dimethyl-2H,2'H-[3,4']bipyrazolyl-3'-ol

Prepare the title compound from 3-acetyl-4-hydroxy-6-methyl-pyran-2-one and benzylhydrazine dihydrochloride according to the procedure illustrated in Examples 2, 3 and 4.

LCMS (M+H): m/z 269, retention time 1.95 min.

Example 25

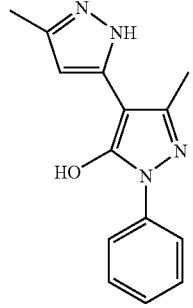

5,5'-Dimethyl-2'-phenyl-2H,2'H-[3,4']bipyrazolyl-3'-ol

Prepare the title compound from 3-acetyl-4-hydroxy-6-methyl-pyran-2-one and phenylhydrazine according to the procedure illustrated in Examples 2, 3 and 4.

LCMS (M+H): m/z 255, retention time 1.77 min.

Example 26

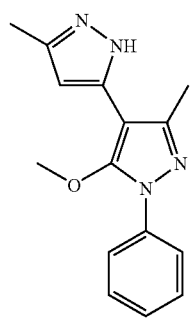

5'-Methoxy-5,3'-dimethyl-1'-phenyl-2H,1'H-[3,4']bipyrazolyl (A)

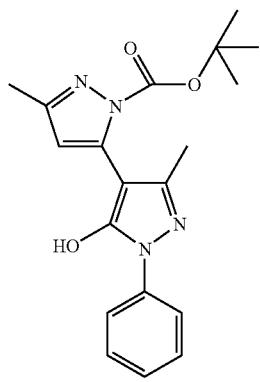

(A) 5'-Hydroxy-5,3-dimethyl-1'-phenyl-1H-[3,4']bipyrazolyl-2-carboxylic acid tert-butyl ester (B) 5-Hydroxy-5,3'-dimethyl-1'-phenyl-1H-[3,4']bipyrazolyl-1-carboxylic acid tert-butyl ester (B)

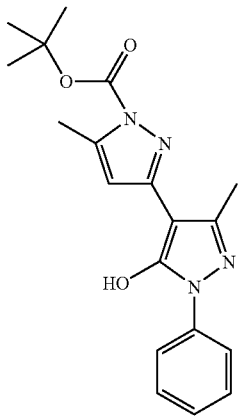

To 5,5'-Dimethyl-2'-phenyl-2H,2'H-[3,4']bipyrazolyl-3'-ol (0.118 g, 0.457 mmol) (Example 25) in ethanol (4 ml) add tert-butyl carbazate (0.120 g, 0.914 mmol). Heat at reflux for 1.5 hours, after which evaporate the ethanol. Chromatography on silica gel, eluting with 50% ethyl acetate/heptane provides 0.101 g of a mixture of positional isomers A and B. Use the mixture for the next step.

LCMS (M+H): m/z 355, retention time 1.97 min. and 3.24 min., respectively.

(C)

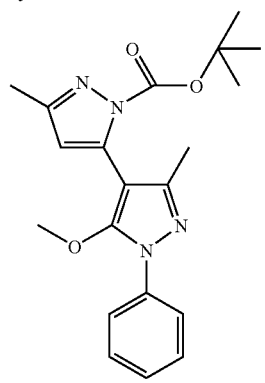

(D)

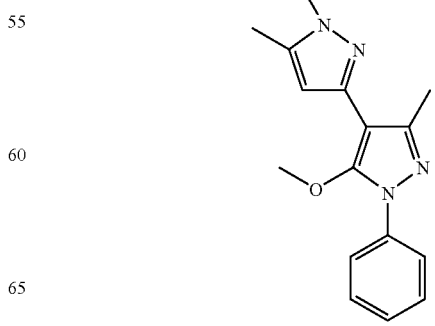

(C) 5'-Methoxy-5,3'-dimethyl-1'-phenyl-1'H-[3,4']bipyrazolyl-2-carboxylic acid tert-butyl ester (D) 5'-Methoxy-5,3'-dimethyl-1'-phenyl-1H-[3,4']bipyrazolyl-1-carboxylic acid tert-butyl ester

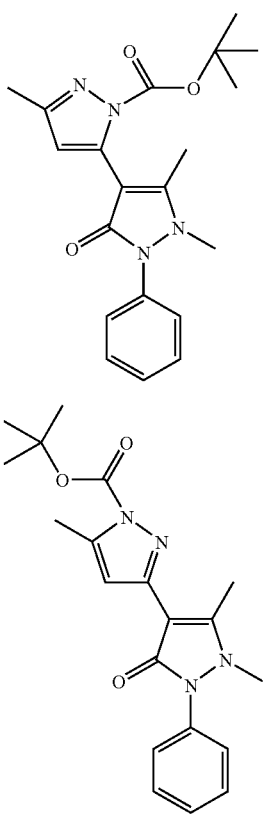

(E) 5,1',5'-Trimethyl-3'-oxo-2'-phenyl-2',3'-dihydro-1'H-[3,4']bipyrazolyl-2-carboxylic acid tert-butyl ester (F) 5,1',5'-Trimethyl-3'-oxo-2'-phenyl-2',3'-dihydro-1'H-[3,4']bipyrazolyl-1-carboxylic acid tert-butyl ester To a mixture of compounds (A) and (B) (0.100 g, 0.282 mmol) in DMF (5 ml) add NaHCO₃ (0.071 g, 0.845 mmol) and iodomethane (0.40 g, 2.82 mmol). Stir the mixture at room temperature overnight. Dilute the reaction mixture with ethyl acetate (25 ml), wash with water (30 ml×5), and dry (sodium sulfate). Chromatography on silica gel, eluting with 50% ethyl acetate/heptane provided 0.013 g of O-methylated products ((C) and (D) LCMS (M+H): m/z 369, retention time 3.30 min.) and 0.012 g of N-methylated products ((E) and (F), LCMS (M+H): m/z 369, retention time 2.63 min.). Use the O-methylated products for the next step.

5'-Methoxy-5,3'-dimethyl-1'-phenyl-2H,1'H-[3,4']bipyrazolyl

To the mixture of O-methylated products, compounds (C) and (D) (0.013 g 0.035 mmol), in dichloromethane (1 ml) add trifluoroacetic acid (1 ml). Stir this mixture at room temperature for 1 hour, and then evaporate the mixture to dryness. Dilute the residue with dichloromethane, wash sequentially with water, aqueous sodium bicarbonate solution, and water. Dry the organic layer (sodium sulfate) and concentrate to give 0.006 g (0.022 mmol) of the title compound.

LCMS (M+H): m/z 269, retention time 2.83 min.

Example 27

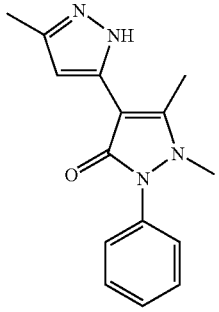

5,1',5'-Trimethyl-2'-phenyl-1',2'-dihydro-2H-[3,4']bipyrazolyl-3'-one

To the mixture of the N-methyl isomers (E) and (F) of Example 26 (0.012 g, 0.035 mmol) in dichloromethane (1 ml) add trifluoroacetic acid (1 ml). Stir this mixture at room temperature for 1 hour, and then evaporate the mixture to dryness. Dilute the residue with dichloromethane, wash sequentially with water, aqueous sodium bicarbonate solution, and water. Dry the organic layer (sodium sulfate) and concentrate to give 0.009 g (0.035 mmol) of the title compound.

LCMS (M+H): m/z 269, retention time 2.06 min.

Example 28

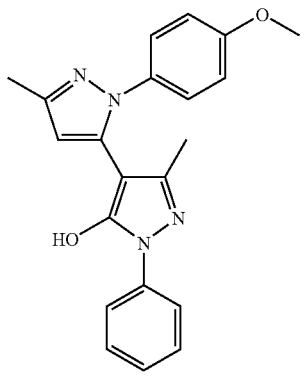

2-(4-Methoxy-phenyl)-5,5'-dimethyl-2'-phenyl-2H,2'H-[3,4']bipyrazolyl-3'-ol

To (4-methoxyphenyl)-hydrazine hydrochloride (0.083 g, 0.48 mmol) in ethanol (5 ml) add sodium bicarbonate (0.067 g, 0.80 mmol) after which stir the mixture for 10 min. Add 1-[1-phenyl-3-methyl-5-oxo-4,5-dihydro-1H-pyrazol-4-yl]-butane-1,3-dione (0.103 g, 0.40 mmol. The mixture was heated at reflux for 1.5 hours after which it was evaporated to dryness. Chromatography on silica gel, eluting with 50 to 100% ethyl acetate/heptane provided 0.071 g of the title compound.

LCMS (M+H): m/z 361, retention time 2.43 min.

Example 29

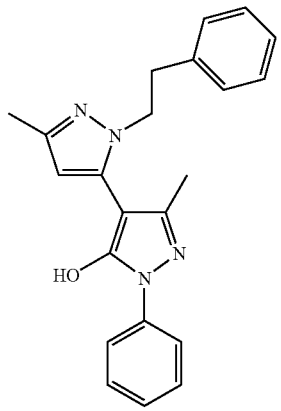

5,5'-Dimethyl-2-phenethyl-2'-phenyl-2H,2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and phenethyl hydrazine sulfate according to the procedure of Example 28.

LCMS (M+H): m/z 359, retention time 2.55 min.

Example 30

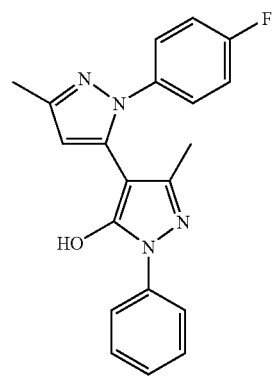

2-(4-Fluoro-phenyl)-5,5'-dimethyl-2'-phenyl-2H,2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and 4-fluorophenyl hydrazine hydrochloride according to the procedure of Example 28.

LCMS (M+H): m/z 349, retention time 2.48 min.

Example 31

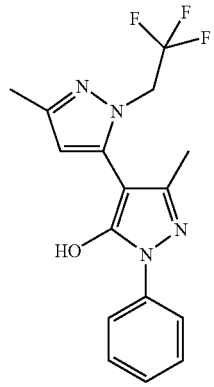

5,5'-Dimethyl-2'-phenyl-2-(2,2,2-trifluoro-ethyl)-2H,2'H-[3,4']bipyrazolyl-3'-ol Prepare the title compound from 1-[1-phenyl-3-methyl-5-oxo-4,5-dihydro-1H-pyrazol-4-yl]-butane-1,3-dione and 2,2,2-trifluoro-ethyl hydrazine (70% in water) according to the procedure of Example 28.

LCMS (M+H): m/z 337, retention time 2.35 min.

Example 32

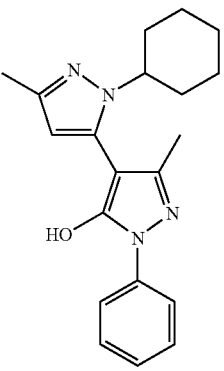

2-Cyclohexyl-5,5'-dimethyl-2'-phenyl-2H,2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and cyclohexylhydrazine hydrochloride according to the procedure of Example 28.

LCMS (M+H): m/z 337, retention time 2.50 min.

Example 33

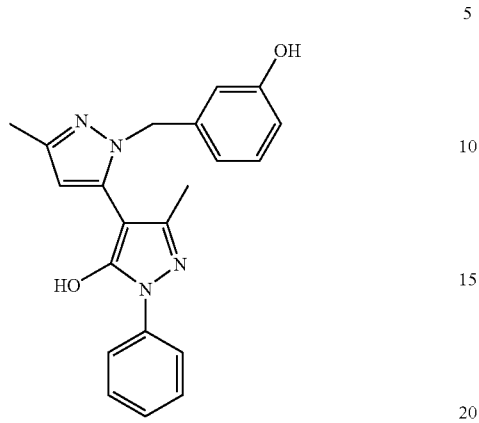

2-(3-Hydroxy-benzyl)-5,5'-dimethyl-2'-phenyl-2H, 2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and 3-hydroxybenzyl hydrazine dihydrochloride according to the procedure of Example 28.

LCMS (M+H): m/z 361, retention time 2.18 min.

Example 34

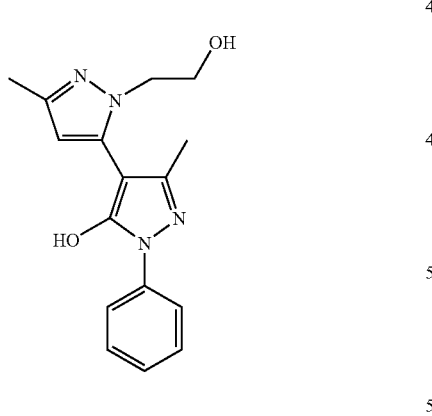

2-(2-Hydroxy-ethyl)-5,5'-dimethyl-2'-phenyl-2H, 2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and 2-hydroxy-ethyl hydrazine according to the procedure of Example 28.

LCMS (M+H): m/z 299, retention time 1.83 min.

Example 35

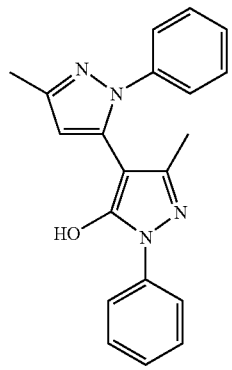

5,5'-Dimethyl-2,2'-diphenyl-2H,2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and phenyl hydrazine according to the procedure of Example 28.

LCMS (M+H): m/z 331, retention time 2.42 min.

Example 36

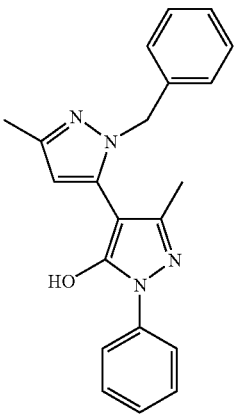

2-Benzyl-5,5'-dimethyl-2'-phenyl-2H,2'H-[3,4']bipyrazolyl-3'-ol

Prepare the compound from 1-[1-phenyl-3-methyl-5-oxo-4,5-dihydro-1H-pyrazol-4-yl]-butane-1,3-dione and benzylhydrazine hydrochloride according to the procedure of Example 28.

LCMS (M+H): m/z 345, retention time 2.69 min.

Example 37

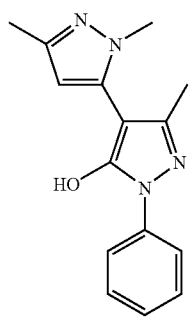

2,5,5'-Trimethyl-2'-phenyl-2H,2'H-[3,4']bipyrazolyl-3'-ol

Prepare the title compound from 1-[1-phenyl-3-methyl-5-oxo-4,5-dihydro-1H-pyrazol-4-yl]-butane-1,3-dione and methylhydrazine according to the procedure of Example 28.

LCMS (M+H): m/z 269, retention time 2.10 min.

Example 38

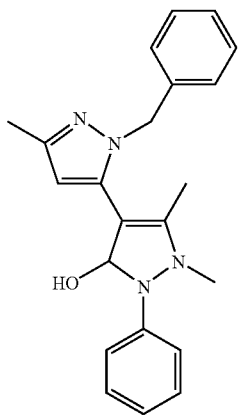

2-Benzyl-5,1',5'-trimethyl-2'-phenyl-1',2'-dihydro-2H-[3,4']bipyrazolyl-3'-one

To 2-benzyl-5,5'-dimethyl-2'-phenyl-2H,2'H-[3,4']bipyrazolyl-3'-ol (Example 36, 0.200 g, 0.58 mmol) in DMF add cesium carbonate (0.944 g, 2.90 mmol), and then iodomethane (0.823 g, 5.8 mmol). Stir this mixture at room temperature overnight. Dilute the reaction mixture with ethyl acetate, wash with water (25 ml×5) and dry (sodium sulfate). Chromatograph on silica gel, eluting with 50-100% ethyl acetate/heptane to provide 0.045 g of the title compound.

LCMS (M+H): m/z 359 with retention time 2.84 min.

The reaction also affords an O-methyl compound. See Example 39 below.

Example 39

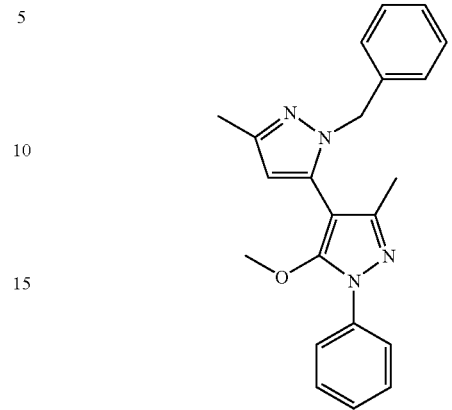

2-Benzyl-5-methoxy-5,3'-dimethyl-1-phenyl-2H,1'H-[3,4']bipyrazole

Isolate the title compound from the chromatography described in Example 38 to afford 0.033 g of O-methylated isomer.

LCMS (M+H): m/z 359 with retention time 3.51 min.

What is claimed is:

1. A compound of formula I:

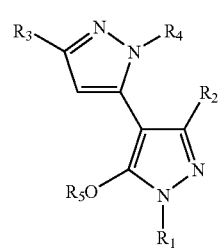

I wherein:

$R_1$ is selected from the group consisting of aryl, benzyl, $C_{3-8}$cycloalkyl, straight chain $C_{1-10}$alkyl, $C_{3-8}$cycloalkyl$C_{1-6}$alkyl, arylcarbonyl, aryl$C_{1-6}$alkyl$C_{3-8}$cycloalkylcarbonyl, and $C_{1-10}$alkylcarbonyl;

wherein said aryl, or benzyl is optionally substituted with one or more substituents each independently selected from $C_{1-6}$alkyl, $C_{1-6}$perfluoroalkyl, halogen, hydroxy, $C_nH_xF_y$alkoxy wherein n is 1-4, x is 0-8, y is 1-9 and x+y is 2n+1, $C_1$-$C_6$alkoxy, nitro, or aryl;

$R_2$ is selected from the group consisting of $C_{1-6}$alkyl, $C_{3-8}$cycloalkyl, and aryl wherein said aryl is optionally substituted with one or more substituents each independently selected from $C_{1-6}$alkyl, $C_{1-6}$perfluoroalkyl, halogen, hydroxy, $C_nH_xF_y$alkoxy wherein n is 1-4, x is 0-8, y is 1-9 and x+y is 2n+1, $C_1$-$C_6$alkoxy, nitro, or aryl;

$R_3$ is selected form the group consisting of aryl, $C_{3-8}$cycloalkyl, $C_{1-6}$alkyl and hetero-aryl wherein said aryl or hetero-aryl is optionally substituted with one or more substituents each independently selected from $C_{1-6}$alkyl, $C_{1-6}$perfluoroalkyl, halogen, hydroxy, $C_nH_xF_y$alkoxy wherein n is 1-4, x is 0-8, y is 1-9 and x+y is 2n+1, $C_1$-$C_6$alkoxy, nitro, or aryl;

R₄ is selected form the group consisting of H, aryl, arylC$_{2-6}$alkyl, benzyl, C$_{1-6}$perfluoroalkyl, C$_{3-8}$cycloalkyl and C$_{1-6}$alkyl wherein said aryl is selected from phenyl, biphenyl, anthracenyl, phenanthrenyl, fluorenyl, indenyl, pentenyl, azulenyl, biphenylenyl and partially hydrogenated derivatives of the same, and said aryl or benzyl is optionally substituted with one or more substituents each independently selected from C$_{1-6}$alkyl, C$_{1-6}$perfluoroalkyl, halogen, hydroxy, C$_n$H$_x$F$_y$alkoxy wherein n is 1-4, x is 0-8, y is 1-9 and x+y is 2n+1, C$_1$-C$_6$alkoxy, or aryl;

R₅ is H, C$_{1-6}$alkyl, or C$_{3-8}$cycloalkyl; and with the proviso that (a) when R₁ and R₄ are phenyl or 4-chlorophenyl, and R₅ is hydrogen then R₂ and R₃ are other than methyl simultaneously;

(a) when R₁ is phenyl or 4-chlorophenyl and R₄ and R₅ are hydrogen then R₂ and R₃ are other than methyl simultaneously, or a stereoisomer or pharmaceutically acceptable salt thereof.

2. The compound according to claim 1 wherein
R₁ is selected from the group consisting of aryl, benzyl, C$_{3-8}$cycloalkyl, straight chain C$_{1-10}$alkyl, and arylC$_{1-6}$alkyl;
R₂ and R₃ are C$_{1-6}$alkyl; and
R₅ is hydrogen or C$_{1-6}$alkyl.

3. The compound according to claim 1 wherein
R₁ is aryl;
R₂ and R₃ are C$_{1-6}$alkyl;
R₄ is hydrogen; and
R₅ is hydrogen or C$_{1-6}$alkyl.

4. The compound according to claim 3 selected from the group consisting of:
2'-(2-Fluoro-phenyl)-5,5'-dimethyl-2H,2'H-[3,4']bipyrazolyl-3'-ol, 2'-(4-Isopropyl-phenyl)-5,5'-dimethyl-2H, 2'H-[3,4']bipyrazolyl-3'-ol, 2'-(4-Fluoro-phenyl)-5,5'-dimethyl-2H,2'H-[3,4']bipyrazolyl-3'-ol, 5,5'-Dimethyl-2'-(4-trifluoromethyl-phenyl)-2H,2'H-[3,4'] bipyrazolyl-3'-ol, 5,5'-Dimethyl-2'-(4-methoxy-phenyl)-2H,2'H-[3,4']bipyrazolyl-3'-ol, 2'-(3-Fluoro-phenyl)-5,5'-dimethyl-2H,2'H-[3,4']bipyrazolyl-3'-ol, 2'-(2-Methyl-phenyl)-5,5'-dimethyl-2H,2'H-[3,4']bipyrazolyl-3'-ol, 5,5'-Dimethyl-2'-(4-trifluoromethoxy-phenyl) -2H,2'H-[3,4']bipyrazolyl-3'-ol, 5,5'-Dimethyl-2'-(4-methyl-phenyl) -2H,2'H-[3,4']bipyrazolyl-3'-ol, 5,5'-Dimethyl-2'-(3-methyl-phenyl)-2H,2'H-[3,4']bipyrazolyl-3'-ol, 5,5'-Dimethyl-2'-(2-ethyl-phenyl)-2H, 2'H-[3,4']bipyrazolyl-3'-ol, 5,5'-Dimethyl-2'-(3,4-dichloro-phenyl)-2H,2'H-[3,4']bipyrazolyl-3'-ol, 5,5'-Dimethyl-2'-(3-chlorophenyl)-2H,2'H-[3,4'] bipyrazolyl-3'-ol, 2'-(4-tert-Butyl-phenyl)-5,5'-dimethyl-2H,2'H-[3,4']bipyrazolyl-3'-ol, 5,5'-Dimethyl-2'-(3-trifluoromethyl-phenyl)-2H,2'H-[3,4'] bipyrazolyl-3'-ol, and 5'-Methoxy-5,3'-dimethyl-1'-phenyl-2H,1'H-[3,4']bipyrazolyl.

5. The compound according to claim 1 wherein
R₁ is aryl;
R₂ and R₃ are C$_{1-6}$alkyl;
R₄ is arylC$_{2-6}$alkyl, or benzyl; and
R₅ is hydrogen or C$_{1-6}$alkyl.

6. The compound according to claim 5 which is selected from the group consisting of:
5,5'-Dimethyl-2-phenethyl-2'-phenyl-2H,2'H-[3,4']bipyrazolyl-3'-ol, 2-Benzyl-5,5'-dimethyl-2'-phenyl-2H, 2'H-[3,4']bipyrazolyl-3'-ol, and 2-Benzyl-5'-methoxy-5,3'-dimethyl-1-phenyl-2H,1'H-[3,4]bipyrazole, and 2-(3-Hydroxy-benzyl)-5,5'-dimethyl-2'-phenyl-2H, 2'H-[3,4']bipyrazolyl-3'-ol.

7. The compound according to claim 1 wherein
R₁ is aryl;
R₂ and R₃ are C$_{1-6}$alkyl;
R₄ is C$_{3-8}$cycloalkyl or C$_{1-6}$alkyl and
R₅ is hydrogen.

8. The compound according to claim 7 which is selected from the group consisting of:
5,5'-Dimethyl-2'-phenyl-2-(2,2,2-trifluoro-ethyl)-2H,2'H-[3,4']bipyrazolyl-3'-ol, 2-Cyclohexyl-5, 5'-dimethyl-2'-phenyl-2H,2'H-[3,4']bipyrazolyl-3'-ol, and 2,5,5'-Trimethyl-2'-phenyl-2H, 2'H-[3,4']bipyrazolyl-3'-ol.

9. The compound according to claim1 wherein
R₁ is aryl;
R₂ and R₃ are C$_{1-6}$alkyl;
R₄ is aryl; and
R₅ is hydrogen.

10. The compound according to claim 9 which is selected from the group consisting of:
2-(4-Methoxy-phenyl)-5,5'-dimethyl-2'-phenyl-2H,2'H-[3,4']bipyrazolyl-3'-ol and 2-(4-Fluoro-phenyl)-5,5'-dimethyl-2'-phenyl-2H,2'H-[3,4']bipyrazolyl-3'-o.

11. The compound according to claim 1 wherein
R₁ is arylC$_{2-6}$alkyl or benzyl;
R₂ and R₃ are C$_{1-6}$alkyl; and
R₄ and R₅ are hydrogen.

12. The compound according to claim 11 which is selected from the group consisting of 5,5'-Dimethyl-2'-phenethyl-2H, 2'H-[3,4']bipyrazolyl-3'-ol, 2'-(3-Hydroxy-benzyl)-5,5'-dimethyl-2H,2'H-[3,4']bipyrazolyl-3'-ol, and 2'-Benzyl-5, 5'-dimethyl-2H,2'H-[3,4']bipyrazolyl-3'-ol.

13. The compound according to claim 1 wherein
R₁ is C$_{3-8}$cycloalkyl;
R₂ and R₃ are C$_{1-6}$alkyl; and
R₄ and R₅ are hydrogen.

14. The compound according to claim 13 which is 2'-Cyclohexyl-5,5'-dimethyl-2H-2'H-[3,4]bipyrazolyl-3'-ol.

15. A compound which is 5,1',5'-trimethyl-2'-phenyl-1',2'-dihydro-2H-[3,4']bipyrazolyl-3'-one.

16. A pharmaceutical composition comprising an effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 8,053,458 B2  Page 1 of 1
APPLICATION NO. : 11/855521
DATED : November 8, 2011
INVENTOR(S) : Kosley et al.

It is certified that error appears in the above-identified patent and that said Letters Patent is hereby corrected as shown below:

On the title page, in item (75), in "Inventors", line 2, delete "MacDonald" and insert -- Macdonald --.

Signed and Sealed this
Twentieth Day of November, 2012

David J. Kappos
*Director of the United States Patent and Trademark Office*